US012698307B2

(12) United States Patent
Stone et al.

(10) Patent No.: US 12,698,307 B2
(45) Date of Patent: Aug. 4, 2026

(54) CELLULAR DELIVERY METHODS

(71) Applicant: PYC Therapeutics Limited, Nedlands (AU)

(72) Inventors: Shane Stone, Coolbellup (AU); Clinton Hall, Langford (AU); Anja Stirnweiss, Subiaco (AU); Paula Cunningham, Subiaco (AU)

(73) Assignee: PYC Therapeutics Limited, Nedlands (AU)

( * ) Notice: Subject to any disclaimer, the term of this patent is extended or adjusted under 35 U.S.C. 154(b) by 1080 days.

(21) Appl. No.: 17/786,671

(22) PCT Filed: Dec. 18, 2020

(86) PCT No.: PCT/AU2020/051397
§ 371 (c)(1),
(2) Date: Jun. 17, 2022

(87) PCT Pub. No.: WO2021/119756
PCT Pub. Date: Jun. 24, 2021

(65) Prior Publication Data
US 2023/0048338 A1      Feb. 16, 2023

(30) Foreign Application Priority Data
Dec. 20, 2019    (AU) ................................ 2019904882

(51) Int. Cl.
| | |
|---|---|
| C07K 14/00 | (2006.01) |
| A61K 31/712 | (2006.01) |
| A61K 47/42 | (2017.01) |
| A61K 47/64 | (2017.01) |

(52) U.S. Cl.
CPC .......... C07K 14/001 (2013.01); A61K 31/712 (2013.01); A61K 47/42 (2013.01); A61K 47/64 (2017.08)

(58) Field of Classification Search
CPC .. C07K 14/001; C07K 2319/09; C07K 14/47; C07K 14/00
See application file for complete search history.

(56) References Cited

U.S. PATENT DOCUMENTS

| | | | |
|---|---|---|---|
| 6,551,795 B1 | 4/2003 | Rubenfield et al. | |
| 6,858,396 B2 | 2/2005 | Dix | |
| 2006/0107345 A1 | 5/2006 | Alexandrov et al. | |
| 2007/0044171 A1 | 2/2007 | Kovalic et al. | |
| 2016/0340683 A1 | 11/2016 | Eudes et al. | |

FOREIGN PATENT DOCUMENTS

| | | |
|---|---|---|
| CN | 103096932 A | 5/2013 |
| RU | 2670488 C2 | 10/2018 |
| WO | 2001081581 A2 | 11/2001 |
| WO | 2018223092 A1 | 12/2018 |
| WO | 2021/119756 A1 | 6/2021 |
| WO | 2025/043278 A1 | 3/2025 |

OTHER PUBLICATIONS

Bolognesi, Benedetta, et al. "Single point mutations induce a switch in the molecular mechanism of the aggregation of the Alzheimer's disease associated Aβ42 peptide." ACS Chemical Biology 9.2 (2014): 378-382. (Year: 2014).*
Wang, Xiaoling, et al. "Potential aggregation prone regions in biotherapeutics: a survey of commercial monoclonal antibodies." MAbs. vol. 1. No. 3. Taylor & Francis, 2009. (Year: 2009).*
Sawai, Monali V., et al. "Impact of single-residue mutations on the structure and function of ovispirin/novispirin antimicrobial peptides." Protein engineering 15.3 (2002): 225-232. (Year: 2002).*
https://www.uniprot.org/uniprotkb/A0A1I3UCK6/entry, accessed Mar. 12, 2026, published Nov. 22, 2017 (Year: 2017).*
Agard et al., "A Strain-Promoted [3+2] Azide-Alkyne Cycloaddition for Covalent Modification of Biomolecules in Living Systems," Journal of the American Chemical Society (2004) 126(46), pp. 15046-15047.
Betts et al., "Pip6-PMO, A New Generation of Peptide-oligonucleotide Conjugates With Improved Cardiac Exon Skipping Activity for DMD Treatment," Molecular Therapy—Nucleic Acids (2012) 1, e38, pp. 1-13.
Chandler et al., "Liver-Directed Adeno-Associated Virus Serotype 8 Gene Transfer Rescues a Lethal Murine Model of Citrullinemia Type 1," Gene Therapy (2013) 20:1188-1191.
Correa, "Considerations and Protocols for the Synthesis of Custom Protein Labeling Probes," (2015) Methods Mol. Biol. 1266:55-79.
Dommerholt et al., "Strain-Promoted 1,3-Dipolar Cycloaddition of Cycloalkynes and Organic Azides," Topics in Current Chemistry (2016) 374(2), pp. 1-20.
Erazo-Oliveras et al., "Protein Delivery into Live Cells by Incubation with an Endosomolytic Agent," Nat Methods. (2014), 11:861-867.
Flynn et al., "Antisense Oligonucleotide-Mediated Terminal Intron Retention of the SMN2 Transcript," Mo. Ther. Nucleic Acids (Jun. 1, 2018) 11:91-102.
Hillig et al., "Discovery of Potent SOS1 Inhibitors that Block RAS Activation via Disruption of the RAS-SOS1 Interaction," PNAS (2019) vol. 116, No. 7, pp. 2551-2560.
Hoffmann et al., "A Platform for Discovery of Functional Cell-Penetrating Peptides for Efficient Multi-Cargo Intracellular Delivery," Sci Rep. (Aug. 22, 2018), 8(1):12538, pp. 1-16.

(Continued)

*Primary Examiner* — Lianko G Garyu
*Assistant Examiner* — David Paul Bowles
(74) *Attorney, Agent, or Firm* — McCarter & English, LLP; Marcie B. Clarke

(57) ABSTRACT

An isolated, non-naturally occurring cell-penetrating peptide (CPP) comprising the amino acid sequence:

[SEQ ID NO: 1]
RRSRTARAGRPGRNSSRPSAPR and sequences which have at least 60% similarity to SEQ ID NO: 1.

13 Claims, 3 Drawing Sheets

Specification includes a Sequence Listing.

(56) References Cited

OTHER PUBLICATIONS

International Preliminary Report on Patentability for International PCT Application No. PCT/AU2020/051397 dated Aug. 23, 2021.
International Search Report for International PCT Application No. PCT/AU2020/051397 dated Feb. 2, 2021.
Karpel-Massler et al., "A Synthetic Cell-Penetrating Dominant-Negative ATF5 Peptide Exerts Anticancer Activity against a Broad System of Treatment-Resistant Cancers," (2016) Clin Cancer Res., 22(18):4698-4711.
Leshchiner et al., "Direct Inhibition of Oncogenic KRAS by Hydro-carbon-Stapled SOS1 Helices," Proc Natl Acad Sci USA (2015) 112(6):1761-1766.
Milech et al., "GFP-Complementation Assay to Detect Functional CPP and Protein Delivery into Living Cells," Sci. Rep. (2015) 5:18329, pp. 1-11.
Qureshi, "Beta-Lactamase: An Ideal Reporter System for Monitoring Gene Expression in Live Eukaryotic Cells," (2007) Biotechniques, 42(1):91-96.
Sakamoto et al., "Protacs: Chimeric Molecules that Target Proteins to the Skp1-Cullin-F Box Complex for Ubiquitination and Degradation," Proc. Natl. Acad. Sci. USA (2001) 98(15), pp. 8554-8559.
Singh et al., "A Multi-Exon-Skipping Detection Assay Reveals Surprising Diversity of Splice Isoforms of Spinal Muscular Atrophy Genes," PLoS One (2012) 7(11):e49595, pp. 1-17.
Stone et al., "Beta-Lactamase Tools for Establishing Cell Internalization and Cytosolic Delivery of Cell Penetrating Peptides," Biomolecules (2018) 8:51-62.
Summerton et al., "Morpholino Antisense Oligomers: Design, Preparation, and Properties," Antisense & Nucleic Acid Drug Development (1997) 7(3), pp. 187-195.
Written Opinion for International PCT Application No. PCT/AU2020/051397 dated Feb. 2, 2021.
Wu et al., "Cell-Penetrating Peptides as Transporters for Morpholino Oligomers: Effects of Amino Acid Composition on Intracellular Delivery and Cytotoxicity," Nucleic Acids Research (2007), vol. 35, No. 15: 5182-5191.
Zakeri et al., "Peptide Tag Forming a Rapid Covalent Bond to a Protein, Through Engineering a Bacterial Adhesin," Proc. Natl. Acad. Sci. USA (2012) 109(12):E690-E697.
Anastasas et al., Cell penetrating peptides for the delivery of ASOs to the neural retina across rodents and NHPs. Platform IPC. Poster, Aug. 28, 2023.
Anastasiadou et al., Cobomarsen, an Oligonucleotide Inhibitor of miR-155, Slows DLBCL Tumor Cell Growth In Vitro and In Vivo. Clin Cancer Res. Feb. 15, 2021;27(4):1139-1149.
Beg et al., Phase I study of MRX34, a liposomal miR-34a mimic, administered twice weekly in patients with advanced solid tumors. Invest New Drugs. Apr. 2017;35(2):180-188.
Cardoso et al., Antibody-conjugated nanoparticles for therapeutic applications. Curr Med Chem. 2012;19 (19):3103-27.
Chang et al., Role of specific endocytic pathways in electrotransfection of cells. Mol Ther Methods Clin Dev. Dec. 17, 2014;1:14058, 8 pages.
Chen et al., Engineering Cell-Permeable Proteins through Insertion of Cell-Penetrating Motifs into Surface Loops. ACS Chem Biol. Sep. 18, 2020;15(9):2568-2576.
Chen et al., Exosomes, a New Star for Targeted Delivery. Front Cell Dev Biol. Oct. 8, 2021;9:751079, 20 pages.
Chen et al., Fusion protein linkers: property, design and functionality. Adv Drug Deliv Rev. Oct. 2013;65(10):1357-69.
Chi et al., Safety of antisense oligonucleotide and siRNA-based therapeutics. Drug Discov Today. May 2017;22 (5):823-833.
Daige et al., Systemic delivery of a miR34a mimic as a potential therapeutic for liver cancer. Mol Cancer Ther. Oct. 2014;13(10):2352-60.
Derakhshankhah et al., Cell penetrating peptides: A concise review with emphasis on biomedical applications. Biomed Pharmacother. Dec. 2018;108:1090-1096.

Doti et al., Recent Applications of Retro-Inverso Peptides. Int J Mol Sci. Aug. 12, 2021;22(16):8677, 21 pages.
Dzierlega et al., Optimization of antisense-mediated exon skipping for Duchenne muscular dystrophy. Gene Ther. Sep. 2020;27(9):407-416.
Fan et al., The Absolute Calibration of a Small-Angle Scattering Instrument with a Laboratory X-ray Source. Journal of Physics. 2010;247:012005, 10 pages.
Fletcher et al., RNA therapeutics in the treatment of retinal disease: delivering the potential. ARVO Annual Meeting 2021, Poster, 1 page, May 3, 2021.
Gallant-Behm et al., A synthetic microRNA-92a inhibitor (MRG-110) accelerates angiogenesis and wound healing in diabetic and nondiabetic wounds. Wound Repair Regen. Jul. 2018;26(4):311-323.
Grainok et al., Antisense Oligomer-mediated Functional Disruption of CNOT3 to Treat PRPF31-associated Retinitis Pigmentosa 11. CBSM, 2019 Combined Biological Sciences Meeting. p. 38, Aug. 30, 2019.
Grupp et al., Chimeric antigen receptor-modified T cells for acute lymphoid leukemia. N Engl J Med. Apr. 18, 2013;368 (16):1509-1518.
Gu et al., PROTACs: An Emerging Targeting Technique for Protein Degradation in Drug Discovery. Bioessays. Apr. 2018;40(4):e1700247, 11 pages.
Guidotti et al., Cell-Penetrating Peptides: From Basic Research to Clinics. Trends Pharmacol Sci. Apr. 2017;38 (4):406-424.
Heitz et al., Twenty years of cell-penetrating peptides: from molecular mechanisms to therapeutics. Br J Pharmacol. May 2009;157(2):195-206.
Hong et al., Effect of D-amino acid substitution on the stability, the secondary structure, and the activity of membrane-active peptide. Biochem Pharmacol. Dec. 1, 1999;58(11):1775-80.
Hong et al., Phase 1 study of MRX34, a liposomal miR-34a mimic, in patients with advanced solid tumours. Br J Cancer. May 2020;122(11):1630-1637.
Huang et al., Expression of P53, P21 in human lung adenocarcinoma A549 cell strains under hypoxia conditions and the effect of TSA on their expression. J Huazhong Univ Sci Technolog Med Sci. 2003;23(4):359-61.
Kawami et al., Characterization of miR-34a-Induced Epithelial-Mesenchymal Transition in Non-Small Lung Cancer Cells Focusing on p53. Biomolecules. Dec. 9, 2021;11(12):1853, 14 pages.
Kumar et al., Prediction of Cell-Penetrating Potential of Modified Peptides Containing Natural and Chemically Modified Residues. Front Microbiol. Apr. 12, 2018;9:725, 10 pages.
Langel, Cell Penetrating Peptides, Methods and Protocols, Third Edition. Humana Press, John M. Walker (Ed.). 627 pages, (2022).
Lebedeva et al., Phosphorothioate Oligodeoxynucleotides as Inhibitors of Gene Expression: Antisense and Non-antisense Effects. Applications of Antisense Therapies to Restenosis. Perspectives in Antisense Science, vol. 3. Klewer Academic. Chapter 6, pp. 99-118, (1999).
Luo et al., Fabrication of self-assembling D-form peptide nanofiber scaffold d-EAK16 for rapid hemostasis. Biomaterials. Mar. 2011;32(8):2013-20.
Maeda et al., Engineering of functional chimeric protein G-Vargula luciferase. Anal Biochem. Jul. 1, 1997;249 (2):147-52.
Malik et al., Extracellular vesicles mediated exocytosis of antisense peptide nucleic acids. Mol Ther Nucleic Acids. Aug. 8, 2021;25:302-315.
Malik et al., Investigation of PLGA nanoparticles in conjunction with nuclear localization sequence for enhanced delivery of antimiR phosphorothioates in cancer cells in vitro. J Nanobiotechnology. Apr. 22, 2019;17(1):57, 13 pages.
Malik et al., Next generation miRNA inhibition using short anti-seed PNAs encapsulated in PLGA nanoparticles. J Control Release. Nov. 10, 2020;327:406-419.
Martin et al., Cell penetrating peptides for the delivery of ASOs to the neural retina across rodents and NHPs. IPC QLD 2023 Platform, 1 page, (2023).

(56)             References Cited

OTHER PUBLICATIONS

Millis et al., VP-001 as an interventional therapy for patients with PRPF31 mutation-associated retinal dystrophy. TIDES USA, 1 page, (2023).

Moulton et al., Cellular uptake of antisense morpholino oligomers conjugated to arginine-rich peptides. Bioconjug Chem. Mar.-Apr. 2004;15(2):290-9.

Mudumba et al., Cell penetrating peptides for the delivery of ASOs to the neural retina across rodents and NHPs. TIDES Oligonucleotide & Peptide Therapeutics. 1 page, May 14-17, 2024.

Muller et al., Spliceosomal peptide P140 for immunotherapy of systemic lupus erythematosus: results of an early phase II clinical trial. Arthritis Rheum. Dec. 2008;58(12):3873-83.

Nouws et al., MicroRNA miR-24-3p reduces DNA damage responses, apoptosis, and susceptibility to chronic obstructive pulmonary disease. JCI Insight. Jan. 25, 2021;6(2):e134218, 17 pages.

O'Brien et al., Overview of MicroRNA Biogenesis, Mechanisms of Actions, and Circulation. Front Endocrinol (Lausanne). Aug. 3, 2018;9:402, 12 pages.

Orlando, Modification of proteins and low molecular weight substances with hydroxyethyl starch (HES). Dissertation. 191 pages, (2003).

Pakula et al., Genetic analysis of protein stability and function. Annu Rev Genet. 1989;23:289-310.

Pratt et al., The RNA-induced silencing complex: a versatile gene-silencing machine. J Biol Chem. Jul. 3, 2009;284 (27):17897-901.

PYC Therapeutics, Creation of a novel gene therapy delivery technology. ASX Announcement. 4 pages, Sep. 8, 2020.

Quinonez et al., Citrullinemia Type I. NCBI Bookshelf. Retrieved online at: https://www.ncbi.nlm.nih.gov/books/NBK1458/. 33 pages, Jul. 7, 2004.

Ruczynski et al., Cell-penetrating peptides as a promising tool for delivery of various molecules into the cells. Folia Histochem Cytobiol. 2014;52(4):257-69.

Rui et al., MicroRNA-34a suppresses breast cancer cell proliferation and invasion by targeting Notch1. Exp Ther Med. Dec. 2018;16(6):4387-4392.

Seto et al., Cobomarsen, an oligonucleotide inhibitor of miR-155, co-ordinately regulates multiple survival pathways to reduce cellular proliferation and survival in cutaneous T-cell lymphoma. Br J Haematol. Nov. 2018;183(3):428-444.

Shi et al., Characterization of a p53/miR-34a/CSF1R/STAT3 Feedback Loop in Colorectal Cancer. Cell Mol Gastroenterol Hepatol. 2020;10(2):391-418.

Sivori et al., CpG and double-stranded RNA trigger human NK cells by Toll-like receptors: induction of cytokine release and cytotoxicity against tumors and dendritic cells. Proc Natl Acad Sci U S A. Jul. 6, 2004;101(27):10116-21.

Slabakova et al., Alternative mechanisms of miR-34a regulation in cancer. Cell Death Dis. Oct. 12, 2017;8(10): e3100, 10 pages.

Smith et al., The Endosomal Escape of Nanoparticles: Toward More Efficient Cellular Delivery. Bioconjug Chem. Feb. 20, 2019;30(2):263-272.

Statello et al., Gene regulation by long non-coding RNAs and its biological functions. Nat Rev Mol Cell Biol. Feb. 2021;22(2):96-118.

Stirnweiss et al., Efficient Delivery of Antisense Oligonucleotides using Cell Penetrating Peptides Enables Potent, Durable Exon Skipping in Mouse and Human Disease Models. 17 Annual Meeting of the Oligonucleotide Therapeutics Society. Poster, 1 page, Sep. 26-29, 2021.

Terra et al., Structural and functional behavior of biologically active monomeric melittin. J Mol Graph Model. Mar. 2007;25(6):767-72.

Tokuriki et al., Stability effects of mutations and protein evolvability. Curr Opin Struct Biol. Oct. 2009;19(5):596-604.

UniProtKB/TrEMBL, Accession No. A0A0X3NSB7. 1 page, Apr. 13, 2016.

UniProtKB/TrEMBL, Accession No. A0A5K1G2B0. 1 page, Dec. 11, 2019.

Van Den Berg et al., Protein transduction domain delivery of therapeutic macromolecules. Curr Opin Biotechnol. Dec. 2011;22(6):888-93.

Verdurmen et al., Cationic cell-penetrating peptides induce ceramide formation via acid sphingomyelinase: implications for uptake. J Control Release. Oct. 15, 2010;147(2):171-9.

Viridian, miRagen Announces Internal Review of Preliminary Topline Data for the Phase 2 SOLAR Clinical Trial of Cobomarsen in Patients with Cutaneous T-Cell Lymphoma (CTCL). Press Release, 2 pages, Oct. 5, 2020.

Viteri et al., An innovative mesothelioma treatment based on miR-16 mimic loaded EGFR targeted minicells (TargomiRs). Transl Lung Cancer Res. Feb. 2018;7(Suppl 1):S1-S4.

Vladar et al., Characterization of nanoparticles by scanning electron microscopy. Characterization of Nanoparticles. Elsevier. Chapter 2.1.1, pp. 7-27, (2020).

Wahane et al., Dual-Modality Poly-l-histidine Nanoparticles to Deliver Peptide Nucleic Acids and Paclitaxel for In Vivo Cancer Therapy. ACS Appl Mater Interfaces. Sep. 29, 2021;13(38):45244-45258.

Wang et al., Tumor penetrating peptides inhibiting MYC as a potent targeted therapeutic strategy for triple-negative breast cancers. Oncogene. Jan. 2019;38(1):140-150.

Woodward et al., Enhancement of Antisense Oligomer Cell Penetration in Retinal Layers Using a Modular Cell Penetrating Peptide Platform. 18th Annual Meeting of the Oligonucleotide Therapeutics Society. Poster, 1 page, Oct. 2-5, 2022.

Wu, MicroRNA and Cancer, Methods and Protocols. Humana Press, John M. Walker (Ed.). 272 pages, (2011).

Yamakuchi et al., MiR-34, SIRT1 and p53: the feedback loop. Cell Cycle. Mar. 1, 2009;8(5):712-5.

Yang, Using an in-vacuum CCD detector for simultaneous small- and wide-angle scattering at beamline X9. J Synchrotron Radiat. Mar. 2013;20(Pt 2):211-8.

Yi et al., SIRT1 and p53, effect on cancer, senescence and beyond. Biochim Biophys Acta. Aug. 2010;1804(8):1684-9.

Zhang et al., MicroRNA-34 family: a potential tumor suppressor and therapeutic candidate in cancer. J Exp Clin Cancer Res. Feb. 4, 2019;38(1):53, 13 pages.

Zhang et al., The growth of siRNA-based therapeutics: Updated clinical studies. Biochem Pharmacol. Jul. 2021;189:114432, 29 pages.

Zhao et al., Intracellular cargo delivery using tat peptide and derivatives. Med Res Rev. Jan. 2004;24(1):1-12.

Zogg et al., Current Advances in RNA Therapeutics for Human Diseases. Int J Mol Sci. Mar. 1, 2022;23(5):2736, 23 pages.

* cited by examiner

SEQUENCE LISTING

<160> NUMBER OF SEQ ID NOS: 3

<210> SEQ ID NO 1

-continued

```
<211> LENGTH: 22
<212> TYPE: PRT
<213> ORGANISM: Artificial Sequence
<220> FEATURE:
<223> OTHER INFORMATION: Synthetic sequence

<400> SEQUENCE: 1

Arg Arg Ser Arg Thr Ala Arg Ala Gly Arg Pro Gly Arg Asn Ser Ser
1               5                   10                  15

Arg Pro Ser Ala Pro Arg
            20

<210> SEQ ID NO 2
<211> LENGTH: 25
<212> TYPE: DNA
<213> ORGANISM: Homo sapiens

<400> SEQUENCE: 2
actttccttc ttttttattt tgtct                                       25

<210> SEQ ID NO 3
<211> LENGTH: 22
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: is Aminohexanoic acid
<220> FEATURE:
<221> NAME/KEY: misc_feature
<222> LOCATION: (5)..(5)
<223> OTHER INFORMATION: is beta-Alanine
<220> FEATURE:
<221> NAME/KEY: misc_feature
<222> LOCATION: (8)..(8)
<223> OTHER INFORMATION: is beta-Alanine
<220> FEATURE:
<221> NAME/KEY: misc_feature
<222> LOCATION: (16)..(16)
<223> OTHER INFORMATION: is Aminohexanoic acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: is Aminohexanoic acid
<220> FEATURE:
<221> NAME/KEY: misc_feature
<222> LOCATION: (22)..(22)
<223> OTHER INFORMATION: is beta-Alanine

<400> SEQUENCE: 3

Arg Xaa Arg Arg Xaa Arg Arg Xaa Arg Tyr Gln Phe Leu Ile Arg Xaa
1               5                   10                  15

Arg Xaa Arg Xaa Arg Xaa
            20
```

CELLULAR DELIVERY METHODS

TECHNICAL FIELD

The present disclosure generally is directed to cell penetrating peptides and related compositions.

BACKGROUND ART

Peptides are attractive diagnostic and therapeutic agents due to their high potency and target specificity. However, one of the challenges to more widespread adoption of peptides as therapeutics is the inability of most peptides to access different tissues within organs (such as the eye), as the various tissue layers generally acts as a barrier to intracellular entry of peptides. Further, existing peptides and any associated cargo typically become entrapped in the cellular endosomal and lysosomal compartments.

Cell-penetrating peptides (CPPs) are a class of peptides that facilitate cellular intake/uptake of various molecular cargoes (from nanosize particles to small chemical molecules, other peptides, proteins, oligonucleotides and fragments of DNA). The "cargo" is associated with the peptides either through chemical linkage via covalent bonds or through non-covalent interactions. The function of the CPPs is to deliver the cargo into cells, a process that commonly occurs through endocytosis. Current use is limited by a lack of cell specificity in CPP-mediated cargo delivery.

The failure of most in vitro validated CPP modalities in vivo, is evidenced by the lack of CPP-delivered drugs in the clinic. The problem is that stepping from single cell entry in vitro into the in vivo setting significantly increases the complexity of the problem of CPP-mediated delivery. Canonical CPPs such as R8, Tat and Penetratin show uptake in vitro, and in vivo as evidenced by fluorescently labelled CPP tracking. However, when coupled to therapeutic cargoes, none of these examples has translated to meaningful functional changes in pathologies. It appears that the utility of CPP-mediated cargo delivery is limited by existing peptides and any associated cargo typically become entrapped in the cellular endosomal and lysosomal compartments, combined with a lack of cell specificity.

In vivo, linear CPPs comprising charge dense cationic peptides with contiguous positively charged amino acids are known to be sequestered by carbohydrate-binding, entrapped in endosomes/lysosomes, and have been demonstrated to bind phospholipid head groups causing membrane deformation. Enhancement of CPP activity by increasing their amphipathic character, a known design strategy for increasing in vitro uptake, does not improve in vivo delivery, perhaps due to the toxicity caused by increased membrane deformation and disruption.

Furthermore, the ubiquitous presence of trypsin and serine endopeptidases, and other proteases in vivo causes rapid degradation of cationic-rich peptides.

Thus, in order to fully exploit the advantages of cell-penetrating peptide delivered therapeutics, there is an ongoing need to develop compositions and methods for delivery of peptides and associated payloads to tissues in vivo, and specific tissues within organs.

The present invention seeks to provide improved or alternative cell penetrating peptides.

The previous discussion of the background art is intended to facilitate an understanding of the present invention only. The discussion is not an acknowledgement or admission that any of the material referred to is or was part of the common general knowledge as at the priority date of the application.

SUMMARY OF INVENTION

The present invention provides an isolated, non-naturally occurring cell-penetrating peptide (CPP) comprising the amino acid sequence:

[SEQ ID NO: 1]
RRSRTARAGRPGRNSSRPSAPR and sequences which have at least 60% similarity to SEQ ID NO: 1.

The sequences of the invention may have at least 65%, 70%, 75%, 80%, or 85% similarity and preferably at least about 90, 95% or 98% similarity at the amino acid level to SEQ ID NO: 1.

Preferably, the CPP is modified by one or more of the following: use of non-canonical amino acids, fatty acids, detectable labels, oligonucleotides, cholesterol, and reactive groups.

Preferably, the CPP is conjugated to a molecule of interest. The molecule of interest may be chosen from the following: a therapeutic agent, an oligonucleotide, a further peptide or protein, a reactive group, a fatty acid, cholesterol, or a detectable label. Preferably, the conjugation is carried out using: a covalent link, or a non-covalent interaction.

The present invention further provides a modified cell comprising the CPP of SEQ ID NO: 1 and sequences which have at least 60% similarity to SEQ ID NO: 1 or the CPP of SEQ ID NO: 1 and sequences which have at least 60% similarity to SEQ ID NO: 1 conjugated to a molecule of interest.

The present invention further provides for use of the CPP of SEQ ID NO: 1 and sequences which have at least 60% similarity to SEQ ID NO: 1, the CPP of SEQ ID NO: 1 and sequences which have at least 60% similarity to SEQ ID NO: 1 conjugated to a molecule of interest or a modified cell comprising either of these in the manufacture of a medicament or diagnostic agent.

Use of the CPP of SEQ ID NO: 1 and sequences which have at least 60% similarity to SEQ ID NO: 1, the CPP of SEQ ID NO: 1 and sequences which have at least 60% similarity to SEQ ID NO: 1 conjugated to a molecule of interest or a modified cell comprising either of these as a medicament or diagnostic agent.

A kit comprising (i) the CPP of SEQ ID NO: 1 and sequences which have at least 60% similarity to SEQ ID NO: 1, the CPP of SEQ ID NO: 1 and sequences which have at least 60% similarity to SEQ ID NO: 1 conjugated to a molecule of interest or a modified cell comprising either of these; and (ii) instructions for use.

BRIEF DESCRIPTION OF THE DRAWINGS

Further features of the present invention are more fully described in the following description of several non-limiting embodiments thereof. This description is included solely for the purposes of exemplifying the present invention. It should not be understood as a restriction on the broad summary, disclosure or description of the invention as set out above. The description will be made with reference to the accompanying drawings in which.

DESCRIPTION OF INVENTION

Detailed Description of the Invention

Cell Penetrating Peptides

Figure 1:
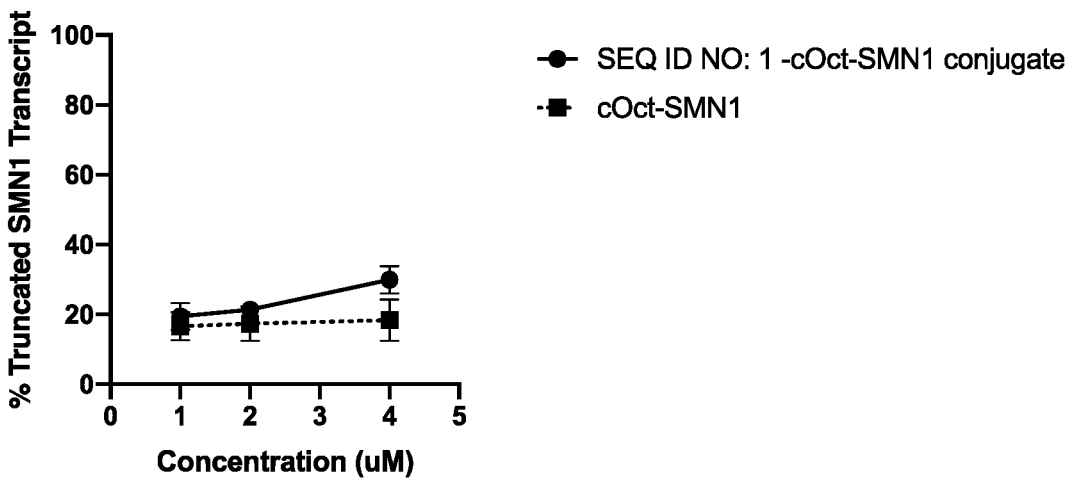
FIG. 1 is a graph of the efficacy of SMN1 exon 7-skipping 48 h post-treatment with peptide-SMN1 conjugate and SMN1 only.

Cell penetrating peptide (CPP) characteristics, e.g. linear CPPs comprising charge dense cationic peptides with contiguous positively charged amino acids, responsible for enhanced in vitro performance, often does not translate to in vivo outcomes. CPP efficacy is closely associated with toxicity, and a fine balance is required between efficacy and toxicity for both successful in vitro and in vivo CPPs. One of the key hurdles to overcome is the entrapment of the CPP-cargo moiety within endosomes and lysosomes. Here we present an assay which requires localisation of the CPP-cargo to the nucleus to effect a functional readout, and thus if effective, demonstrates endosomal/lysosomal escape and/or nuclear delivery. We have identified CPPs that provide successful delivery of a cargo to the nucleus of the cell, such as an amino acid sequence including an antisense oligonucleotide.

Accordingly, there is provided an isolated, non-naturally occurring cell-penetrating peptide (CPP) comprising the amino acid sequence:

[SEQ ID NO: 1]
RRSRTARAGRPGRNSSRPSAPR and sequences which have at least 60% similarity to SEQ ID NO: 1.

Preferably, the CPP comprises between 10 and 100 residues. For example, the CPP may comprise between 10 and 50 residues, 20 to 30 residues, 20 to 40 residues, 30 to 70 residues, 40 to 60 residues or 25 to 50 residues.

The SEQ ID NO: 1 amino acid sequence analogues include those having an amino acid sequence wherein one or more of the amino acids is substituted with another amino acid, which substitutions do not substantially alter the biological activity (cell penetrating ability) of the molecule. These amino acid sequence analogues preferably have conservative amino acid substitutions when compared to SEQ ID NO: 1.

In the context of the invention, an analogous sequence is taken to include a CCP amino acid sequence which has at least 60%, 65%, 70%, 75%, 80%, or 85% similarity and preferably at least about 90, 95% or 98% similarity at the amino acid level over at least 20, 21, 22, 23, 24, 25, 26, 27, 28, 29, 30, 35, 40, 45, 50, 100 or 200 amino acids, with the amino acid sequence set out in SEQ ID NO: 1. In particular, similarity should typically be considered with respect to those regions of the sequence known to be essential for the function of the CPP encoded by SEQ ID NO: 1, rather than non-essential neighbouring sequences.

The analogous sequences may have a sequence that has at least about 60%, 65%, 70%, 75%, 80%, 85% identity and preferably at least about 90%, 95% or 98% identity to SEQ ID NO: 1 (i.e. identical residues). The analogous sequences may have a sequence that has at least about 60%, 65%, 70%, 75%, 80%, 85% similarity and preferably at least about 90%, 95% or 98% similarity to SEQ ID NO: 1 (i.e. residues conserved with similar physicochemical properties.

Similarity comparisons can be conducted by eye, or more usually, with the aid of readily available sequence comparison programs. These commercially available computer programs can calculate % similarity between two or more sequences. The % similarity may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise almost identical pair of sequences, one insertion or deletion will cause the following amino acid residues to be put out of alignment, thus potentially resulting in a large reduction in % similarity and identity when a global alignment is performed. Consequently, most sequence comparison methods are designed to produce optimal alignments that take into consideration possible insertions and deletions without penalising unduly the overall similarity score. This is achieved by inserting "gaps" in the sequence alignment to try to maximise local homology.

Amino acid sequence identity and similarity may be determined using the EMBOSS Pairwise Alignment Algorithms tool available from The European Bioinformatics Institute (EMBL-EBI), which is part of the European Molecular Biology Laboratory. This tool is accessible at the website located at www.ebi.ac.uk/Tools/emboss/align/. This tool utilizes the Needleman-Wunsch global alignment algorithm (Needleman and Wunsch, 1970). Default settings are utilized which include Gap Open: 10.0 and Gap Extend 0.5. The default matrix "Blosum62" is utilized for amino acid sequences and the default matrix.

The term "cell penetrating peptide" (CPP) refers to a peptide that is capable of crossing a cellular membrane. In one example, a CPP is capable of translocating across a mammalian cell membrane and entering into a cell. In another example, a CPP may direct a conjugate to a desired subcellular compartment. Thus, a CPP may direct or facilitate penetration of a molecule of interest across a phospholipid, cellular, mitochondrial, endosomal, lysosomal, vesicular, or nuclear membrane. A CPP may be translocated across the membrane with its amino acid sequence complete and intact, or alternatively partially degraded.

A CPP may direct a molecule of interest from outside a cell through the plasma membrane, and into the cytoplasm or a desired subcellular compartment. Alternatively, or in addition, a CPP may direct a molecule of interest across the blood-brain, trans-mucosal, hematoretinal, skin, gastrointestinal and/or pulmonary barriers.

The ability of a CPP to translocate across membranes may be energy dependent or independent, and/or receptor dependent or independent. In some examples, the CPP is a peptide which is demonstrated to translocate across a plasma membrane as determined by the methods described herein. CPPs encompass: (i) peptides that become internalized by cells but subsequently entrapped within endosomes or lysosomes;

and (ii) peptides that not only become internalized by cells, but also are able to escape endosomal and/or lysosomal compartments once internalized by cells, and in addition are able to mediate intracellular delivery, into the cytosol and nucleus, mitochondria, Golgi-apparatus, and other intracellular compartments.

In some examples, a peptide will comprise between one and two, one and five, or ten conservative amino acid substitutions relative to any sequence described herein, e.g, 1, 2, 3, 4, 5, 6, 7, 8, 9, 10, 11, 12, 13, 14, 15, 16, 17, 18 19 or 20 conservative amino acid substitutions. A conservative replacement (also called a conservative mutation or a conservative substitution) is an amino acid replacement in which an amino acid residue is replaced with another amino acid residue having a side chain with similar physicochemical properties resulting in a protein with a different amino acid sequences but that has similar biochemical properties (e.g. charge, hydrophobicity and size).

Amino acid residues having side chains with similar physiochemical properties are known in the art, and include amino acids with basic side chains (e.g, lysine, arginine, histidine), acidic side chains (e.g, aspartic acid, glutamic acid), uncharged polar side chains (e.g, glycine, asparagine, glutamine, serine, threonine, tyrosine, cysteine, tryptophan), nonpolar side chains (e.g, alanine, valine, leucine, isoleucine, proline, phenylalanine, methionine), beta-branched side 10 chains (e.g, threonine, valine, isoleucine) and aromatic side chains (e.g, tyrosine, phenylalanine, tryptophan, histidine). Conservative amino acid substitutions include those with amino acids, which have been substituted with non-naturally occurring amino acids and non-proteogenic amino acids, which are therefore not among the regular amino acids encoded by the genetic code. Conservative amino acid substitutions further include D-amino acids.

The term "basic amino acid" relates to any amino acid, including natural and non-natural amino acids, that has an isoelectric point above 6.3, as measured according to Kice & Marvell "Modern Principles of organic Chemistry" (Macmillan, 1974) or Matthews and van Holde "Biochemistry" Cummings Publishing Company, 1996. Included within this definition are arginine, lysine, histidine and homoarginine (Har), as well as derivatives thereof. Suitable non-natural basic amino acids are described in U.S. Pat. No. 6,858,396.

In some examples the amino acid sequence of any of the CPP peptides consists of 20 to 100 residues, e.g, 20, 21, 22, 23, 24, 25, 26, 27, 28, 29, 30, 35, 40, 45, 50, 55, 60, 65, 70, 75, 80, 85, 90, 95, or another number of residues from 20 to 100. In other examples the amino acid sequence of any of the foregoing peptides consists of 30 to 70 residues, e.g, 35, 40, 45, 48, 50, 52, 60, 65, or another number of residues from 30 to 70 residues. In other examples the amino acid sequence of any of the foregoing peptides consists of 40 to 60 residues, e.g, 42, 43, 45, 48, 50, 52, 54, 57, 58, or another number of residues from 40 to 60 residues. In some examples, the amino acid sequence of any of the foregoing peptides consists of 35 to 50 residues, e.g, 36, 38, 40, 42, 43, 45, 57, 58, or another number of residues from 35 to 50 residues. In yet other examples the amino acid sequence of any of the foregoing peptides consists of 20 to 50 residues, e.g, 20, 21, 22, 23, 24, 25, 26, 27, 28, 29, 30, 32, 35, 37, 38, 40, 42, 46, 48, or another number of residues from 20 to 50.

In one example the amino acid sequence of the peptide consists of an amino acid sequence corresponding to SEQ ID NO: 1. For the avoidance of doubt, it is to be understood that in such examples, while the amino acid sequence of the peptide consists of an amino acid sequence corresponding to SEQ ID NO: 1, the peptide may, nevertheless, comprise chemical modifications that do not alter the amino acid sequence. Such modifications include, but are not limited to: use of non-canonical amino acids, fatty acids, detectable labels, polynucleotides, cholesterol, and reactive groups; conjugation of the CPP with non-peptide linkers; conjugation of the CPP with molecules of interest (including therapeutic agents, oligonucleotides and detectable labels). In other examples the CPP consists of an amino acid sequence corresponding to SEQ ID NO: 1.

In one embodiment, the CCP comprises multiple copies of an amino acid sequence corresponding to SEQ ID NO: 1 and sequences which have at least 60% similarity to SEQ ID NO: 1, referred to herein as a multimeric peptides. In some examples, a multimeric peptide comprises between two and ten copies of an amino acid sequence corresponding to SEQ ID NO: 1, e.g, 2, 3, 4, 5, 6, 7, 8, 9, or 10 copies of an amino acid sequence corresponding to SEQ ID NO: 1. In one embodiment, the CCP comprises multiple copies of an amino acid sequence corresponding to SEQ ID NO: 1 and sequences which have at least 60% similarity to SEQ ID NO: 1.

Modified CPPs

The CPP may be modified by the use of non-canonical amino acids, fatty acids, detectable labels, polynucleotides, cholesterol, and reactive groups. Such modified peptides may confer additional functionalities to a CPP, such as facilitating detection of peptide entry, localisation within cells, enhanced cell entry, and/or reduced peptide degradation in vitro or in vivo.

Non-Canonical Amino Acids

In some examples the CPP is a modified peptide comprising a non-canonical amino acid. Suitable non-canonical amino acids include, but are not limited to, α-amino-n-butyric acid, norvaline, norleucine, alloisoleucine, t-leucine, ornithine, allothreonine, β-alanine, β-amino-n-butyric acid, n-isopropyl glycine, isoserine, sarcosine, 6-aminohexanoic acid, gamma-aminobutyric acid and 5-aminovaleric acid.

Reactive Groups

In other examples the modified CPP may comprise a reactive group. Suitable reactive groups include, but are not limited to, azide groups, amine-reactive groups, thiol-reactive groups, and carbonyl-reactive groups. In some examples the reactive groups are part of a chemical tag. Suitable chemical tags include, but are not limited to, a SNAP tag, a CLIP tag, a HaloTag or a TMP-tag. In one example, the chemical tag is a SNAP-tag or a CLIP-tag. SNAP and CLIP fusion proteins enable the specific, covalent attachment of virtually any molecule to a protein or peptide of interest as described, for example, in Corrêa 2015 (Methods Mol Biol, 1266:55-79). In another example, the chemical tag is a HaloTag. HaloTag involves a modular protein tagging system that allows different molecules to be covalently linked, either in solution, in living cells, or in chemically fixed cells. In another example, the chemical tag is a TMP-tag. TMP-tags are able to label intracellular, as opposed to cell-surface, proteins with high selectivity.

Fatty Acids

In some examples the modified CPP may comprise a fatty acid. Suitable fatty acids for modified peptides include, but are not limited to, palmitic acid, myristic acid, caprylic acid, lauric acid, n-octanoic acid, and n-decanoic acid.

Cholesterol

In other examples the modified CPP may comprise cholesterol.

Oligonucleotides

In some examples the modified CPP may comprise an oligonucleotide. In such cases, the oligonucleotide may be an antisense oligonucleotide, siRNA, microRNA, an RNAi, a single stranded DNA or RNA oligonucleotide, a double stranded DNA oligonucleotide, an mRNA, or a plasmid.

Detectable Labels

In some examples the modified CPP may comprise a detectable label. The term "detectable label" refers to any type of molecule which can be detected by optical, fluorescent, isotopic imaging or by mass spectroscopic techniques, or by performing simple enzymatic assays. Any detectable label known in the art may be used. In some examples the detectable label is selected from among: a reporter protein, a fluorophore, a fluorogenic substrate, a luminogenic substrate, and a biotin.

The detectable label may be a reporter protein. Suitable reporter proteins include a fluorescent protein as described herein, a β lactamase as described in Qureshi (2007), Biotechniques, 42(1):91-95, a haloalkane dehalogenase, or a luciferase. In some examples the reporter protein comprises the amino acid sequence of a β-lactamese.

The detectable label may be a fluorescent tag. For example, the fluorescent tag may be a fluorophore such as fluorescein isothiocyanate, fluorescein thiosemicarbazide, rhodamine, Texas Red, a CyDye such as Cy3, Cy5 and Cy5.5, a Alexa Fluor such as Alexa488, Alexa555, Alexa594 and Alexa647) or a near infrared fluorescent dye. The fluorescent tag may be a fluorescent protein such as green fluorescent protein (GFP), enhanced green fluorescent protein (EGFP), AcGFP or TurboGFP, Emerald, Azami Green, ZsGreen, EBFP, Sapphire, T-Sapphire, ECFP, mCFP, Cerulean, CyPet, AmCyanl, Midori-Ishi Cyan, mTFPI (Teal), enhanced yellow fluorescent protein (EYFP), Topaz, Venus, mCitrine, YPet, PhiYFP, ZsYellowl, mBanana, Kusabira, ange, mOrange, dTomato, dTomato-Tandem, AsRed2, mRFPI, Jred, mCherry, HcRedl, mRaspberry, HcRedl, HcRed-Tandem, mPlum, AQ 143. The fluorescent tag may be a quantum dot. The fluorescent tag may a pH-sensitive fluorophore such as naphthofluorescein, pHrodo™ Green (ThermoFisher), and pHrodo™ Red (ThermoFisher). Fluorescent tags may be detected using fluorescent microscopes such as epifluorescence or confocal microscopes, fluorescence scanners such as microarray readers, spectrofluorometers, microplate readers and/or flow cytometers.

The detectable label may be a luminogenic substrate. Suitable luminogenic substrates include, but are not limited to, D-Luciferin, L-Luciferin, Coelenterazine.

The detectable label may be an epitope tag. For example, the epitope tag may be a poly-histidine tag such as a hexahistidine tag or a dodecahistidine, a FLAG tag, a Myc tag, a HA tag, a GST tag or a V5 tag. Epitope tags are routinely detected with commercially available antibodies. A person skilled in the art will be aware that an epitope tag may facilitate purification and/or detection. For example, a CPP comprising a hexahistidine tag may be purified using methods known in the art, such as, by contacting a sample comprising the protein with nickel-nitrilotriacetic acid (Ni-NTA) that specifically binds a hexahistidine tag immobilized on a solid or semi-solid support, washing the sample to remove unbound protein, and subsequently eluting the bound protein. Alternatively, or in addition a ligand or antibody that binds to an epitope tag may be used in an affinity purification method.

The detectable label may be a mass tag or an isobaric tag. Such tags may be used for relative absolute quantification (iTRAQ). A mass tag is a chemical label used for mass spectrometry-based quantification of proteins and peptides. In such methods mass spectrometers recognise the mass difference between the labelled and unlabelled forms of a protein or peptide, and quantification is achieved by comparing their respective signal intensities as described, for example, in Bantscheff et al. 2007. Examples of mass tags include TMTzero, TMTduplex, TMTsixplex and TMT 10-plex. An isobaric tag for relative absolute quantification (iTRAQ) is a chemical tag used in quantitative proteomics by tandem mass spectrometry to determine the amount of proteins from different sources in a single experiment as described, for example, in Wiese et al. 2007.

Conjugated Cargoes

A CPP may be conjugated to a molecule of interest (i.e. a "cargo") to increase the delivery of the molecule of interest into a cell. Molecules of interest include: a therapeutic agent, an oligonucleotide, a further peptide or protein, a reactive group, a fatty acid, cholesterol, or a detectable label. The conjugation may be through a covalent bond or non-covalent interactions. For example, a CPP may be conjugated to an oligonucleotide via a "peptide linker". The moiety may be designed to act upon a particular intracellular target or to direct its transport to a particular subcellular compartment.

The molecule of interest may be covalently linked to an amino acid in the CPP peptide. In one example the covalently linked molecule of interest is covalently linked to the N-terminal of the CPP amino acid sequence. In another example the covalently linked molecule of interest is covalently linked to the C-terminal of the CPP amino acid sequence. In other examples, the covalently linked molecule of interest is covalently linked through an amino acid residue side chain of the CPP (e.g, at an internal lysine or cysteine residue). Those skilled in the art, recognise that this can be achieved through a variety of chemical reactions, including but not limited to, peptide bond formation, amide bond formation, linkage via reactive amines, hydrazone formation, disulphide formation, ether bonds, click chemistries (both copper-catalysed and strain promoted), Staudinger reactions, native chemical ligation and conjugation chemistries such as SpyCatcher/SpyTag isopeptide bond formation.

In some examples the molecule of interest is non-covalently linked to the CPP, e.g, via non-covalent interactions between one or more charged amino acid residues in the CPP and one or more functional groups in the molecule of interest that are of opposite charge to the one or more CPP amino acid residues. The non-covalent interaction may be electro-static interactions, van der Waals forces, pi-bond interactions and hydrophobic interactions.

Therapeutic Agent

In some examples, the conjugated molecule of interest may be a therapeutic agent, preferably a small molecule compound (generally less than about 900 daltons in size). In some examples the small molecule therapeutic agent is a chemotherapeutic agent, a cytotoxic molecule, or a cytostatic molecule.

Oligonucleotides

In some examples, the conjugated molecule of interest may be an oligonucleotide. The oligonucleotide may be an antisense oligonucleotide, siRNA, microRNA, an RNAi, a single stranded DNA or RNA oligonucleotide, a double stranded DNA oligonucleotide, an mRNA, or a plasmid. The oligonucleotide may include morpholino oligonucleotides (PMOs), peptide nucleic acids (PNAs), locked nucleic acids (LNAs), and 2'-O-Methyl oligonucleotides. The oligonucleotides may have (i) a modified backbone structure, e.g., a backbone other than the standard phosphodiester linkage found in naturally occurring oligo- and polynucleotides, and/or (ii) modified sugar moieties, e.g., morpholino moieties rather than ribose or deoxyribose moieties.

Peptides or Proteins

In some examples, the conjugated molecule of interest may be a protein or peptide. The protein or peptide may be: a pro-apoptotic peptide, a targeting protein, a cytotoxic protein, an enzymatic protein, a reporter protein, a peptide-based protein-protein interaction inhibitor, a proteolytic targeting chimera (PROTAC) peptide, and a dominant-negative peptide.

In some examples the enzymatic protein may be ASS-1 (Quinonez and Thoene 2004) or Beta-Lactamase (Stone et al 2018); the peptide interaction inhibitor may be a KRAS/SOS-1 protein interaction blocking peptide (e.g. Leshchiner et al 2015); the proteolytic targeting chimera (PROTAC) peptide sequence may be one from Sakamoto et al 2001 or Gu et al. 2018.

In some examples the protein or peptide may be a pro-apoptotic peptide.

In some examples the protein or peptide may be a targeting protein. The targeting protein may provide increased specificity to peptide conjugates by binding to a specific cell surface antigen (e.g., a receptor), which is then internalized into endosomes. Examples of targeting proteins include, but are not limited to, affibodies, scFvs, single chain antibodies, and other selective binding proteins using alternative scaffolds (e.g, peptide aptamers). Alternatively, the targeting protein may be a genomic targeting protein (e.g, a Cas9 genomic targeting protein or a Cpf1 genomic targeting protein).

In other examples the protein or peptide may be a cytotoxic protein (e.g, Bouganin or diphtheria toxin) that induces rapid cell death upon internalization and escape from endosomes.

In some examples the protein or peptide may be a dominant negative peptide. Dominant negative peptides generally act to interfere with one or more functions of a protein from which they are derived and/or with that of an interacting partner of the full-length protein. Typically, they act by interfering with the interaction of a protein and one or more of its binding partners. In some examples the dominant negative transcription factor peptide is an anti-cancer peptide. Suitable anti-cancer peptides include, but are not limited to: Omomyc, an Activating Transcription Factor 5 (ATF5) dominant negative peptide d/n-ATF5-S1 as described in Massler et al (2016), Clin Cancer Res, 22(18): 4698-4711, anti-Ras-p21 dominant negative peptides such as ras-p21 96-110 (PNC-2) and ras-p21 35-47 as described in Adler et al (2008), Cancer Chemother Pharmacol, 62(3): 491-498.

Reactive Groups

In some examples, the conjugated molecule of interest may be a reactive group. Suitable reactive groups include, but are not limited to, azide groups, amine-reactive groups, thiol-reactive groups, and carbonyl-reactive groups. In some examples the reactive groups are part of a chemical tag. Suitable chemical tags include, but are not limited to, a SNAP tag, a CLIP tag, a HaloTag or a TMP-tag. In one example, the chemical tag is a SNAP-tag or a CLIP-tag. SNAP and CLIP fusion proteins enable the specific, covalent attachment of virtually any molecule to a protein or peptide of interest as described, for example, in Corrêa 2015 (Methods Mol Biol, 1266:55-79). In another example, the chemical tag is a HaloTag. HaloTag involves a modular protein tagging system that allows different molecules to be covalently linked, either in solution, in living cells, or in chemically fixed cells. In another example, the chemical tag is a TMP-tag. TMP-tags are able to label intracellular, as opposed to cell-surface, proteins with high selectivity.

Fatty Acids

In some examples, the conjugated molecule of interest may be a fatty acid. Suitable fatty acids for modified peptides include, but are not limited to, palmitic acid, myristic acid, caprylic acid, lauric acid, n-octanoic acid, and n-decanoic acid.

Cholesterol

In some examples, the conjugated molecule of interest may be cholesterol.

Detectable Labels

In some examples the conjugated molecule of interest a detectable label. The detectable label may be any type of molecule which can be detected by optical, fluorescent, isotopic imaging or by mass spectroscopic techniques, or by performing simple enzymatic assays. Any detectable label known in the art may be used. In some examples the detectable label is selected from among: a reporter protein, a fluorophore, a fluorogenic substrate, a luminogenic substrate, and a biotin.

The detectable label may be a reporter protein. Suitable reporter proteins include a fluorescent protein as described herein, a β lactamase as described in Qureshi (2007), Biotechniques, 42(1):91-95, a haloalkane dehalogenase, or a luciferase. In some examples the reporter protein comprises the amino acid sequence of a β-lactamase.

The detectable label may be a fluorescent tag. For example, the fluorescent tag may be a fluorophore such as fluorescein isothiocyanate, fluorescein thiosemicarbazide, rhodamine, Texas Red, a CyDye such as Cy3, Cy5 and Cy5.5, a Alexa Fluor such as Alexa488, Alexa555, Alexa594 and Alexa647) or a near infrared fluorescent dye. The fluorescent tag may be a fluorescent protein such as green fluorescent protein (GFP), enhanced green fluorescent protein (EGFP), AcGFP or TurboGFP, Emerald, Azami Green, ZsGreen, EBFP, Sapphire, T-Sapphire, ECFP, mCFP, Cerulean, CyPet, AmCyanl, Midori-Ishi Cyan, mTFPI (Teal), enhanced yellow fluorescent protein (EYFP), Topaz, Venus, mCitrine, YPet, PhiYFP, ZsYellowl, mBanana, Kusabira, ange, mOrange, dTomato, dTomato-Tandem, AsRed2, mRFPI, Jred, mCherry, HcRedl, mRaspberry, HcRedl, HcRed-Tandem, mPlum, AQ 143. The fluorescent tag may be a quantum dot. The fluorescent tag may a pH-sensitive fluorophore such as naphthofluorescein, pHrodo™ Green (ThermoFisher), and pHrodo™ Red (ThermoFisher). Fluorescent tags may be detected using fluorescent microscopes such as epifluorescence or confocal microscopes, fluorescence scanners such as microarray readers, spectrofluorometers, microplate readers and/or flow cytometers.

The detectable label may be a luminogenic substrate. Suitable luminogenic substrates include, but are not limited to, D-Luciferin, L-Luciferin, Coelenterazine.

The detectable label may be an epitope tag. For example, the epitope tag may be a poly-histidine tag such as a hexahistidine tag or a dodecahistidine, a FLAG tag, a Myc tag, a HA tag, a GST tag or a V5 tag. Epitope tags are routinely detected with commercially available antibodies. A person skilled in the art will be aware that an epitope tag may facilitate purification and/or detection. For example, a CPP comprising a hexahistidine tag may be purified using methods known in the art, such as, by contacting a sample comprising the protein with nickel-nitrilotriacetic acid (Ni-NTA) that specifically binds a hexahistidine tag immobilized on a solid or semi-solid support, washing the sample to remove unbound protein, and subsequently eluting the bound protein. Alternatively, or in addition a ligand or antibody that binds to an epitope tag may be used in an affinity purification method.

The detectable label may be a mass tag or an isobaric tag. Such tags may be used for relative absolute quantification (iTRAQ). A mass tag is a chemical label used for mass spectrometry-based quantification of proteins and peptides. In such methods mass spectrometers recognise the mass difference between the labelled and unlabelled forms of a protein or peptide, and quantification is achieved by comparing their respective signal intensities as described, for example, in Bantscheff et al. 2007. Examples of mass tags include TMTzero, TMTduplex, TMTsixplex and TMT 10-plex. An isobaric tag for relative absolute quantification (iTRAQ) is a chemical tag used in quantitative proteomics by tandem mass spectrometry to determine the amount of proteins from different sources in a single experiment as described, for example, in Wiese et al. 2007.

Synthesis

Any CPP of the present disclosure may be synthesized using a chemical method known to the skilled artisan. For example, synthetic peptides are prepared using known techniques of solid phase, liquid phase, or peptide condensation, or any combination thereof, and can include natural and/or unnatural amino acids.

Any peptide of the present disclosure may be expressed by recombinant means. For example, the nucleic acid encoding the peptide may be placed in operable connection with a promoter or other regulatory sequence capable of regulating expression in cellular system or organism. Typical promoters suitable for expression in bacterial cells include, for example, the lacz promoter, the Ipp promoter, temperature-sensitive λL or λR promoters, T7 promoter, T3 promoter, SP6 promoter or semi-artificial promoters such as the IPTG-inducible tac promoter or lacUV5 promoter. A number of other gene construct systems for expressing the peptides of the invention in bacterial cells are well-known in the art and are described, for example, in Ausubel et al. (1988), and Sambrook et al. (2001).

Numerous expression vectors for expression of recombinant peptides in bacterial cells have been described, and include, for example, PKC3, pKK173-3, pET28, the pCR vector suite (Invitrogen), pGEM-T Easy vectors (Promega), the pL expression vector suite (Invitrogen) or pBAD/thio—TOPO series of vectors containing an arabinose-inducible promoter (Invitrogen), amongst others.

Typical promoters suitable for expression in yeast cells such as, for example, a yeast cell selected from the group comprising *Pichia pastoris, S. cerevisiae* and *S. pombe*, include, but are not limited to, the ADH1 promoter, the GAL1 promoter, the GAL4 promoter, the CUP1 promoter, the PH05 promoter, the nmt promoter, the RPR1 promoter, or the TEF1 promoter.

Expression vectors for expression in yeast cells are preferred and include, for example, the pACT vector (Clontech), the pDBleu-X vector, the pPIC vector suite (Invitrogen), the pGAPZ vector suite (Invitrogen), the pHYB vector (Invitrogen), the pYD 1 vector (Invitrogen), and the pNMT 1, pNMT41, pNMT81 TOPO vectors (Invitrogen), the pPC86-Y vector (Invitrogen), the pRH series of vectors (Invitrogen), pYESTrp series of vectors (Invitrogen).

Preferred vectors for expression in mammalian cells include, for example, the pcDNA vector suite (Invitrogen), the pTARGET series of vectors (Promega), and the pSV vector suite (Promega).

Suitable methods for transforming and transfecting host cells can be found in Sambrook et al. 2001 and other laboratory textbooks. In one example, nucleic acids may be introduced into prokaryotic cells using for example, electroporation or calcium-chloride mediated transformation. In another example, nucleic acids may be introduced into mammalian cells using, for example, microinjection, calcium phosphate or calcium chloride co-precipitation, DEAE-dextran mediated transfection, transfection mediated by liposomes such as by using Lipofectamine (Invitrogen) and/or cellfectin (Invitrogen), PEG mediated DNA uptake, electroporation, transduction by Adenoviuses, Herpesviruses, Togaviruses or Retroviruses and microparticle bombardment such as by using DNA-coated tungsten or gold particles. Alternatively, nucleic acids may be introduced into yeast cells using conventional techniques such as, for example, electroporation, and PEG mediated transformation.

Following production/expression/synthesis, any protein or peptide of the present disclosure can be purified using a method known in the art such as HPLC See e.g, Scopes (In: Protein purification: principles and practice, Third Edition, Springer Verlag, 1994).

Cell Expression

Also described herein is a modified cell comprising any of the CPPs or CPPs conjugated to a molecule of interest described herein.

The present invention therefore provides a modified cell comprising the CPP of SEQ ID NO: 1 and sequences which have at least 60% similarity to SEQ ID NO: 1 or the CPP of SEQ ID NO: 1 and sequences which have at least 60% similarity to SEQ ID NO: 1 conjugated to a molecule of interest.

The present invention further provides for use of the CPP of SEQ ID NO: 1 and sequences which have at least 60% similarity to SEQ ID NO: 1, the CPP of SEQ ID NO: 1 and sequences which have at least 60% similarity to SEQ ID NO: 1 conjugated to a molecule of interest or a modified cell comprising either of these in the manufacture of a medicament or diagnostic agent.

In some examples a modified cell is a prokaryotic cell. In other examples the modified cell is a eukaryotic cell. Suitable eukaryotic cells include yeast cells, and mammalian cells including, but not limited to human cells. In some examples modified mammalian cells are from a cell line. Suitable cell lines include, but are not limited to, ARPE-19, CHO-K1, HEK-293, COS7, HeLa, N2a, and NIH 3T3.

In some examples a modified cell expresses one or more genetically encoded CPPs or CPPs conjugated to a molecule of interest. In other examples a modified cell is a primary mammalian cell.

In other examples a modified cell does not comprise exogenous nucleic acids encoding a CPP or CPP conjugated to a molecule of interest, but is modified by protein transduction of a CPP or CPP conjugated to a molecule of interest.

Preferably the modified cells are eukaryotic cells. More preferably the eukaryotic cells are mammalian cells. Most preferably the mammalian cells are human cells. In some examples the human cells are human stem cells. Such human stem cells include, but are not limited to, embryonic stem cells, induced pluripotent stem cells, and mesenchymal stem cells. In further examples human cells include, but are not limited to, cardiomyocytes, neurons, hepatocytes, and pancreatic islet cells. In other examples, the mammalian cells are cancer cells (e.g., human cancer cells).

Use

The present disclosure also provides any one of the CPPs, CPPs conjugated to a molecule of interest, or modified cells for use as a medicament or diagnostic agent. The present disclosure also provides any one of the CPPs, CPPs conjugated to a molecule of interest, or modified cells for use in the manufacture of a medicament or diagnostic agent.

The present invention therefore provides for use of the CPP of SEQ ID NO: 1 and sequences which have at least 60% similarity to SEQ ID NO: 1, the CPP of SEQ ID NO: 1 and sequences which have at least 60% similarity to SEQ ID NO: 1 conjugated to a molecule of interest or a modified cell comprising either of these in the manufacture of a medicament or diagnostic agent.

The present invention further provides for use of the CPP of SEQ ID NO: 1 and sequences which have at least 60% similarity to SEQ ID NO: 1, the CPP of SEQ ID NO: 1 and sequences which have at least 60% similarity to SEQ ID NO: 1 conjugated to a molecule of interest or a modified cell comprising either of these as a medicament or diagnostic agent.

The sequences of the invention may have at least 65%, 70%, 75%, 80%, or 85% similarity and preferably at least about 90, 95% or 98% similarity at the amino acid level to SEQ ID NO: 1.

Preferably, the CPP is modified by one or more of the following: use of non-canonical amino acids, fatty acids, detectable labels, oligonucleotides, cholesterol, and reactive groups.

Preferably, the CPP is conjugated to a molecule of interest. The molecule of interest may be chosen from the following: a therapeutic agent, an oligonucleotide, a further peptide or protein, a reactive group, a fatty acid, cholesterol, or a detectable label. Preferably, the conjugation is carried out using: a covalent link, or a non-covalent interaction.

Kits

The present disclosure also provides a kit comprising a CPP of the present invention and instructions for use.

The present invention therefore provides a kit comprising (i) the CPP of SEQ ID NO: 1 and sequences which have at least 60% similarity to SEQ ID NO: 1, the CPP of SEQ ID NO: 1 and sequences which have at least 60% similarity to SEQ ID NO: 1 conjugated to a molecule of interest or a modified cell comprising either of these; and (ii) instructions for use.

The sequences of the invention may have at least 65%, 70%, 75%, 80%, or 85% similarity and preferably at least about 90, 95% or 98% similarity at the amino acid level to SEQ ID NO: 1.

Preferably, the CPP is modified by one or more of the following: use of non-canonical amino acids, fatty acids, detectable labels, oligonucleotides, cholesterol, and reactive groups.

Preferably, the CPP is conjugated to a molecule of interest. The molecule of interest may be chosen from the following: a therapeutic agent, an oligonucleotide, a further peptide or protein, a reactive group, a fatty acid, cholesterol, or a detectable label. Preferably, the conjugation is carried out using: a covalent link, or a non-covalent interaction.

Definitions

The term "canonical amino acid" refers to an amino acid encoded directly by the codons of the universal genetic code. The canonical amino acids are: Alanine, Arginine, Asparagine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, and Valine.

The term "endogenous" or "endogenously encoded" in reference to a nucleotide or amino acid sequence indicates that sequence in question is native to a virus, cell, or organism that has not been experimentally modified to encode or express the amino acid sequence in question.

The term "non-naturally occurring" in reference to a peptide will be understood to indicate that: (i) there is no endogenous gene or open reading frame that encodes an amino acid sequence consisting of the amino acid sequence of the peptide in question; and (ii) there is no endogenous protein fragment the amino acid sequence of which consists of the peptide in question. For example, a peptide consisting of the amino acid sequence of a fragment of an endogenously expressed protein is considered a non-naturally occurring peptide if the protein fragment itself is not naturally expressed or does not ordinarily occur as a byproduct of the endogenously expressed protein.

The term "peptide" is intended to include compounds composed of amino acid residues linked by amide bonds. A peptide may be natural or unnatural, ribosome encoded or synthetically derived. Typically, a peptide will consist of between 2 and 200 amino acids. For example, the peptide may have a length in the range of 10 to 20 amino acids or 10 to 30 amino acids or 10 to 40 amino acids or 10 to 50 amino acids or 10 to 60 amino acids or 10 to 70 amino acids or 10 to 80 amino acids or 10 to 90 amino acids or 10 to 100 amino acids, including any length within said range(s). The peptide may comprise or consist of fewer than about 150 amino acids or fewer than about 125 amino acids or fewer than about 100 amino acids or fewer than about 90 amino acids or fewer than about 80 amino acids or fewer than about 70 amino acids or fewer than about 60 amino acids or fewer than about 50 amino acids.

Peptides, as referred to herein, include "inverso" peptides in which all L-amino acids are substituted with the corresponding D-amino acids, and "retro-inverso" peptides in which the sequence of amino acids is reversed and all L-amino acids are replaced with D-amino acids.

Peptides may comprise amino acids in both L- and/or D-form. For example, both L- and D-forms may be used for different amino acids within the same peptide sequence. In some examples the amino acids within the peptide sequence are in L-form, such as natural amino acids. In some examples the amino acids within the peptide sequence are a combination of L- and D-form. In some examples the amino acids within the peptide sequence are all in D-form.

Peptides may be synthesized using well known solid phase peptide synthesis techniques, and purification techniques.

The term "protein" shall be taken to include a single polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical bond or a disulfide bond. Examples of non-covalent bonds include hydrogen bonds, ionic bonds, Van der Waals forces, and hydrophobic interactions.

General

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (eg. Size, displacement and field strength etc). A range of values will be understood to include all values within the range, including the values defining the range, and values adjacent to the range which lead to the same or substantially the same outcome as the values immediately adjacent to that value which defines the boundary to the range. Accordingly, unless indicated to the contrary, the numerical parameters set forth in the specification and claims are approximations that may vary depending upon the desired properties sought to be obtained by the present invention. Hence "about 80%" means "about 80%" and also "80%". At the very least, each numerical parameter should be construed in light of the number of significant digits and ordinary rounding approaches.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs. The term "active agent" may mean one active agent, or may encompass two or more active agents.

The following examples serve to more fully describe the manner of using the above-described invention, as well as to set forth the best modes contemplated for carrying out various aspects of the invention. It is understood that these methods in no way serve to limit the true scope of this invention, but rather are presented for illustrative purposes.

EXAMPLES

Further features of the present invention are more fully described in the following non-limiting Examples. This description is included solely for the purposes of exemplifying the present invention. It should not be understood as a restriction on the broad description of the invention as set out above.

Example 1

Potential CPP peptides were linked to a phosphorodiamidate oligonucleotide (PMO) that targets exon 7 of the SMN1 gene (Flynn et al 2018), using strain-promoted (SPAAC) click chemistry (Agard et al 2004, Dommerholt et al. 2016). Peptide-PMO conjugates were incubated on ARPE-19 cells for 2 days in full media. Efficacy of internalization was measured by the degree of exon7 skipping in the SMN1 gene RNA transcript through RNA extraction. Peptide-PMOs with % d7 transcript higher than the PMO treatment alone were considered CPPs.

Introduction to the In Vitro CPP-SMN1 Assay

The survival motor neuron (SMN1) gene is ubiquitously expressed and plays important roles in the assembly of the spliceosome and biogenesis of ribonucleoproteins. The splicing regulation of the SMN1 gene has been elucidated (Singh et al 2012.). A splice variant of SMN1, where exon-7 is skipped is a known isoform that results in a shorter SMN protein, denoted D7-SMN1. Exon-skipping, using cell-penetrating peptide delivered phosphorodiamidate morpholino oligomers (PMOs) has been established as a viable route to test CPP efficacy (Wu et al. 2007).

Using the SMN1 gene, we built an exon-skipping assay targeting the SMN1 gene (Flynn et al 2018) at exon-7 using a phosphorodiamidate morpholino oligonucleotide (PMO) conjugated to different CPPs. This assay was used to identify CPPs that could efficiently deliver PMO cargo to the nucleus and effect exon-skipping of SMN1. Efficiency of delivery and function was determined by measuring the change in D7-SMN1 RNA transcript, using RNA extraction, cDNA generation and PCR using SMN1-specific primers. Efficiency was interpreted by the higher the percentage D7-SMN1 transcript, the better the delivery to the nucleus by the CPP.

Given the nature of this assay, the characteristics of natural L-peptides are undesirable due to protease digestion in the presence of full-media. To adequately assess the peptide CPP capacity, peptides were synthesized as either mixed-L/D amino acid containing peptides, where all basic residues were D-amino acids, or as full-D amino acid containing peptides. Both approaches protected peptides from proteolytic degradation during incubation on cells.

Methods

Mammalian Tissue Culture

ARPE-19 cells were obtained from the ATCC (ATCC® CRL-2302). Cell lines were maintained in a humidified incubator at 37° C. with 5% $CO_2$ and cultured in complete medium (DMEM/F12 1:1, 10% FCS; 10 mM HEPES, 1× GlutaMAX™, Pen/Strep 100 u/ml; Gibco, Thermo Fisher Scientific, Waltham, MA, USA)

Peptide and PMO Synthesis, and PPMO Conjugation

CPPs were synthesised using standard Fmoc SPPS based methods (Pepscan GmbH, Lelystad, The Netherlands, and Mimotopes, Mulgrave, VIC, Australia). All sequences contained a C-terminal Azidolysine residue to allow coupling to the PMO; all N-termini were acetylated and C-termini amidated.

The SMN1 PMO (ACTTTCCTTCTTTTTTAT-TTTGTCT) [SEQ ID NO: 2], with a 5' cyclooctyne handle was produced by Gene Tools (Gene Tools LLC, Philomath, OR, USA), using the method developed by Summerton and Weller (1997).

CPP peptides with C-terminal Azidolysine were chemoselectively conjugated with 5'-cyclooocytyne PMO using strain-promoted click chemistry (SPAAC; Agard et al. 2004; Dommerholt et al. 2016). The cycloaddition reaction between the azido-functionalised peptide and the cyclooocytyne-functionalised PMO was carried out for 3-4 days at 37° C. in Phosphate Buffered Saline with 5% DMSO. Peptide-PMO (PPMO) conjugates were separated from unreacted material by ion exchange chromatography (IEX) and desalted. Final fractions were analysed by analytical reverse phase HPLC and LC/MS.

In Vitro SMN1 Efficacy Assay

Exon skipping assays and PCR detection were performed according to published protocols (Mann et al 2002, *Gene Med*, 4, 644-654).

Retinal pigment epithelial cells (ARPE-19) immortalized cells were treated with various concentrations (4 uM, 2 uM, 1 uM, in duplicate) of CPP-PMO conjugate and SMN1 transcript levels assessed 48 h post treatment by RNA extraction and purification, followed by cDNA generation and PCR.

Cells were seeded in 24-well plates (ARPE-19, $2.5\times10^4$ cells/well) in complete medium (DMEM/F12 1:1, 10% FCS; 10 mM HEPES, 1× GlutaMAX™, Pen/Strep 100 u/ml; Gibco, Thermo Fisher Scientific, Waltham, MA, USA). Cells were incubated overnight (37° C., 5% $CO_2$) to allow for cell adherence. On the day of the assay, media was aspirated and replaced with CPP-PMO or PMO only diluted in treatment media (DMEM/F12 1:1, 10% FCS; 10 mM HEPES, 1× GlutaMAX™, Pen/Strep 100 u/ml; Gibco, Thermo Fisher Scientific, Waltham, MA, USA), followed by incubation (37° C., 5% $CO_2$) for 24 h. Fresh media 1:1 was added the following day and cells returned to the incubator for a further 24 h.

48 h post-treatment, the cell media was carefully aspirated, and cells rinsed with PBS. RNA from the treated cells was obtained using commercial RNA extraction kits according to manufacturer's protocol (Bio-Rad Aurum total RNA 96 kit; Quantify RNA yield; Quant-iT RNA BR kit).

Extracted RNA was purified, quantified and then diluted to 10 ng/ul. cDNA was produced using a commercial reverse transcription kit according to the manufacturers protocol (BioRad iScript). The produced cDNA was used as a template with primers designed to amplify region of interest, to amplify the DNA. The efficacy of exon skipping was determined by quantifying full length (FL SMN1) and exon-7 skipped fragment (D7-SMN1) of the SMN1 gene (LC-GX Nucleic Acid Analyzer) and calculating a percentage. The higher the percentage of D7-SMN1 DNA, the greater the CPP delivery efficiency In Vitro SMN1 Viability Assay Cells were seeded in 96-well plates (ARPE-19, $4\times10^3$ cells/well) in complete medium (DMEM/F12 1:1, 10% FCS; 10 mM HEPES, 1× GlutaMAX™, Pen/Strep 100 u/ml; Gibco, Thermo Fisher Scientific, Waltham, MA, USA). Cells were incubated overnight (37° C., 5% $CO_2$) to allow for cell adherence. On the day of the assay, media was aspirated and replaced with CPP-PMO or PMO only diluted in treatment media (DMEM/F12 1:1, 10% FCS; 10 mM HEPES, 1× GlutaMAX™, Pen/Strep 100 u/ml; Gibco, Thermo Fisher Scientific, Waltham, MA, USA) at various concentrations (32, 16, 8, 4, 2, and 1 uM), followed by incubation (37° C., 5% $CO_2$) for 24 h. Fresh media 1:1 was added the following day and cells returned to the incubator for a further 24 h.

48 h post-treatment, viability of the cells was measured using the commercial CellTiter-Glo® Luminescent Cell Viability Assay (Promega, Australia). In brief the CellTiter-Glo reagent lyses the cells and generates a luminescent signal that is proportional to the amount of ATP present, which in turn is directly proportional to the number of live cells present in culture. All assays were conducted with a known cytotoxic agent, melittin (Renata et al. 2007), and cell only control. Cell viability was used to determine the level of toxicity caused by the CPP-PMO conjugates, where high viability equates to low toxicity, and low viability with high toxicity, respectively.

Results

In FIG. 1 and Table 1, at 4 uM, 2 uM and 1 uM the CPP of SEQ ID NO: 1 conjugated to SMN1 PMO creates more truncated D7-SMN1 transcript than the SMN1 PMO alone. The efficacy of induced SMN1 exon-skipping follows a dose-response curve for applied Peptide-PMO conjugate. The Peptide-PMO conjugate is more efficient (1.2-fold at 2 uM) in inducing SMN1 exon-skipping than the SMN1 PMO only treatment. Thus, the peptide described in SEQ ID NO: 1 is an effective cell-penetrating and nuclear delivery agent.

Figure 2:
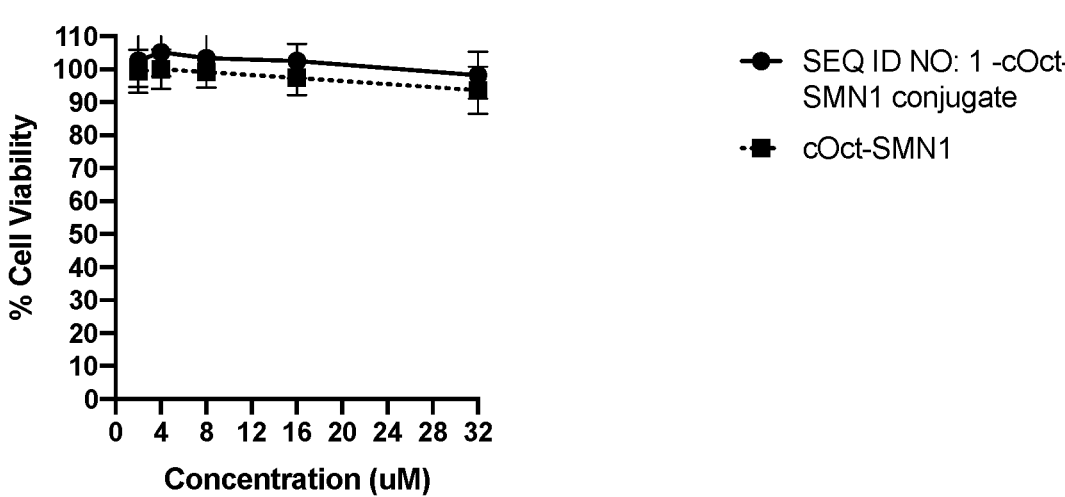
FIG. 2 is a graph of the cell viability 48 h post-treatment with peptide-SMN1 conjugate and SMN1 only.

In FIG. 2 and Table 2, the viability of ARPE-19 cells treated with Peptide-PMO conjugate versus PMO only at 32 uM for 48 hours, clearly shows that the addition of the Peptide-PMO conjugate is less deleterious (1.05-fold) to cell viability than the PMO alone. This indicates that the cell-penetrating and nuclear delivery actions of the peptide are not deleterious to cell health, and do not cause the inherent toxicity typically associated with cationic cell-penetrating peptides.

TABLE 1

| | | Efficacy results of CPP enhanced delivery of SMN1 antisense oligonucleotide | | |
|---|---|---|---|---|
| SEQM | | Percent exon7-skipped SMN1 transcript (±SD) | | |
| ID NO: | Sequence | 4 uM (±SD) | 2 uM (±SD) | 1 uM (±SD) |
| 1[azk]2 | rrsrtaraGrpGrnssrpsapr[azk] ACTTTCCTTCTTTTTTATTTTGTCT | 29.99 (±3.96) | 21.38 (±2.10) | 19.44 (±3.82) |
| 2 | ACTTTCCTTCTTTTTTATTTTGTCT | 18.34 (±5.99) | 17.35 (±4.97) | 16.59 (±4.07) |

TABLE 2

| | | Percent Mean Viability (±SD) | | | | |
|---|---|---|---|---|---|---|
| SEQ ID NO: | Sequence | 32 uM (±SD) | 16 uM (± SD) | 8 uM (± SD) | 4 uM (± SD) | 2 uM (±SD) |
| 1[azk]2 | rrsrtaraGrpGrnssrpsapr[azk]ACTTTCCTTCT TTTTTATTTTGTCT | 98.20 (±7.21) | 102.52 (±5.24) | 103.34 (±8.75) | 105.23 (±7.32) | 102.61 (±7.91) |
| 2 | ACTTTCCTTCTTTTTTATTTTGTCT | 93.61 (±7.14) | 97.42 (±5.23) | 99.11 (±4.66) | 100.01 (±6.03) | 99.41 (±6.53) |

Viability results of CPP enhanced delivery of SMN1 antisense oligonucleotide

Example 2

The in vitro SMN1 efficacy assay described in Example 1 is equally applicable to the in vivo setting, given the ubiquitous distribution of the Smn gene in the mouse body, Smn being the mouse orthologue of the human SMN1. The use of natural L-peptides is undesirable in the in vivo setting, due to presence of a vast array of proteases in the body. To adequately assess the peptide's cell-penetrating capacity, peptides were synthesized as either mixed-L/D amino acid containing peptides, where all basic residues were D-amino acids, or as full-D amino acid containing peptides. Both approaches have been established to protect peptides from proteolytic degradation during systemic administration into animals.

The ability of CPP-PMOs to deliver the Smn cargo in vivo to the RPE cell later in the eye was assessed by administration into the vitreous humor of mice and measuring the change in Smn transcript levels in the retina, RPE and choroid cell layers after 5, 7, 21 and 28 days. The CPP of the present invention (SEQ ID NO: 1) and control CPP Pip6a (SEQ ID NO: 3), conjugated to an Smn PMO (SEQ ID NO: 2), were administered by intravitreal injection at 1.6 ug (0.5 ul volume) per eye. At the desired time point post treatment, the animals were culled and eyes were dissected, tissue layers homogenised and RNA extracted using the same protocol as per Example 1.

The control CPP Pip6a contains non-natural amino acids (X and B):

[SEQ ID NO: 3]
RXRRBRRXRYQFLIRXRBRXRB

Arg Ahx Arg Arg beta-Ala Arg Arg Ahx Arg Tyr Gln

Phe Leu Ile Arg Ahx Arg beta-Ala Arg Ahx Arg beta-Ala

X=Ahx=Aminohexanoic acid; B=beta-Ala=beta-Alanine

The efficiency of delivery and function to the various organs was determined by measuring the change in Smn RNA transcript from full-length to an exon-7 skipped fragment (D7-Smn) RNA transcript, using RNA extraction, cDNA generation and PCR using Smn-specific primers. Efficiency was interpreted by the higher the percentage D7-Smn transcript, the better the delivery to the tissue by the CPP.

Glial fibrillary acidic protein (GFAP) is an intermediate-filament cytoskeletal protein. Levels of GFAP are strongly influenced by injury or stress in some cell types and GFAP expression has become an important marker of injury in the central nervous system. In the eye, Muller glia cells normally express low levels of GFAP which increases considerably following retinal injury. Peptides which elicit relatively increased GFAP expression post intravitreal (IVT) administration are deemed to be more toxic.

Methods

Peptide and PMO Synthesis and Peptide-PMO Conjugation

CPPs were synthesised using standard Fmoc SPPS based methods (Pepscan GmbH, Lelystad, The Netherlands, and Mimotopes, Mulgrave, VIC, Australia). All sequences contained a C-terminal Azidolysine residue to allow coupling to the PMO; all N-termini were acetylated and C-termini amidated.

The Smn PMO (ACTTTCCTTCTTTTTTATTTTGTCT; SEQ ID NO: 2), with a 5' cyclooctyne handle was produced by Gene Tools (Gene Tools LLC, Philomath, OR, USA)

CPP peptides with C-terminal Azidolysine were chemoselectively conjugated with 5'-cycloocytyne PMO using strain-promote click chemistry (SPAAC; Agard et al. 2004; Dommerholt et al. 2016) and purified by Ion Exchange Chromatography and quantified by LC-MS.

In Vivo Smn Efficacy Assay (IVT Administration)

Exon skipping assays and RT-PCR detection were performed according to published protocols (Mann et al 2002, *Gene Med,* 4, 644-654).

Mice (C576/6; age 7 weeks) were sourced from Australian BioResources (ABR). Selected CPP-PMOs were injected into the vitreous at 1.6 ug (0.5 ul) per eye, with one to three mice per treatment group.

48 h post-treatment, mice were culled, and the following ocular tissues harvested; retina, RPE layer or RPE/choroid combined. The tissues were homogenised, and RNA was obtained using commercial RNA extraction kits according to manufacturer's protocol (Bio-Rad Aurum total RNA 96 kit; Quantify RNA yield; Quant-iT RNA BR kit).

Extracted RNA was purified, quantified and then diluted to 10 ng/ul. cDNA was produced using a commercial reverse transcription kit according to the manufacturers protocol (BioRad iScript). The produced cDNA was used as a template with primers designed to amplify region of interest, to amplify the DNA. The efficacy of exon skipping was determined by quantifying full length (FL Smn) and exon-7 skipped fragment (D7-Smn) of the Smn gene (LC-GX Nucleic Acid Analyzer) and calculating a percentage. The higher the percentage of D7-Smn DNA, the greater the CPP delivery efficiency.

GFAP In Vivo Toxicity Assay

Expression of GFAP mRNA was quantified via amplification of cDNA obtained as part of the in vivo Smn efficacy assay described above. ddPCR was performed using BioRad droplet generator and reader (QX200 DG8) and thermocyclers (T100), specific probes for murine Gfap (dM-muCPE5116126) and housekeeping genes Gapdh, Eef1a1 and Rp127 (dMmuCPE5195283, dMmuCPE5101732 and dMmuCPE5197083) as well as ddPCR Master mix for Probes (#1863024) and other ddPCR specific consumables from BioRad (#1863005, 12001925, 1863004, 1864007).

Assay results were obtained by BioRad ddPCR software in copies/uL. This was then normalised to housekeeping genes for comparison across experiments. Peptides which elicit relatively increased GFAP expression are deemed to be more toxic.

Results

Figure 3:
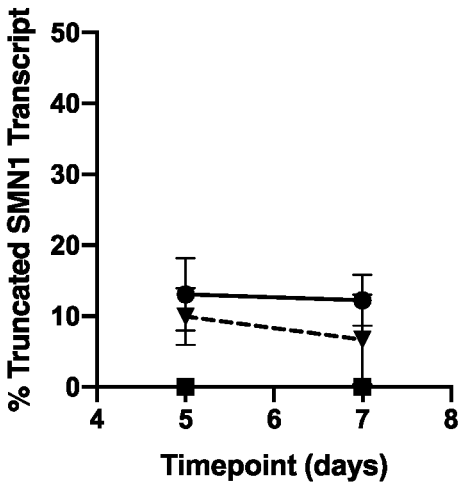
FIG. 3 is graph of the efficacy of Smn exon7-skipping produced by the CPP of SEQ ID NO: 1 conjugated to Smn PMO in vivo in RPE/choroid cells.
Figure 4:
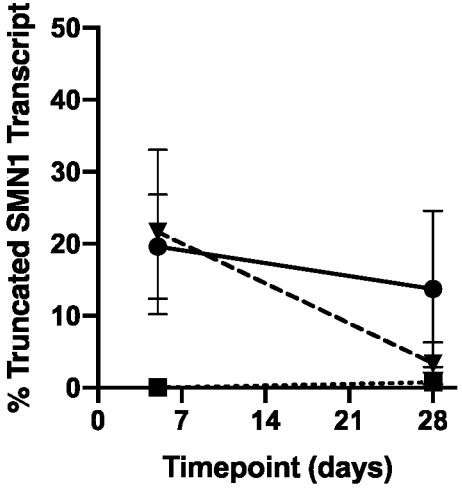
FIG. 4 is graph of the efficacy of Smn exon7-skipping produced by the CPP of SEQ ID NO: 1 conjugated to Smn PMO in vivo in retinal cells.

In FIGS. 3 and 4 and Tables 3 and 4, the CPP of SEQ ID NO: 1 conjugated to Smn PMO creates more truncated D7-Smn transcript than the Smn PMO alone. The Peptide-PMO conjugate is more efficient in inducing Smn exon-skipping than the Smn PMO only treatment, or a competitor CPP Pip6a (Betts et. al. 2012). Thus, the peptide described in SEQ ID NO: 1 is an effective in vivo cell-penetrating and nuclear delivery agent.

Figure 5:
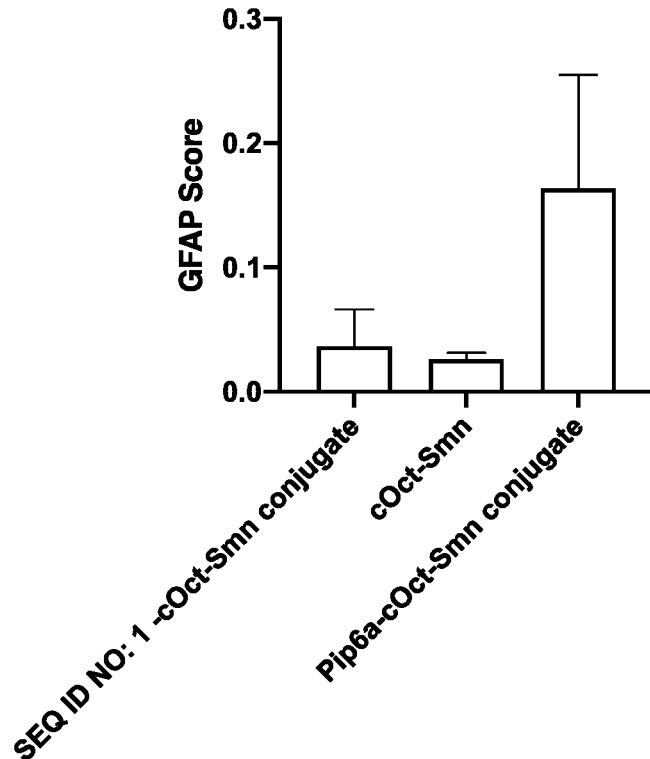
FIG. 5 is a graph of the GFAP in vivo toxicity of the CPP of SEQ ID NO: 1 conjugated to Smn PMO five days post-injection.

In FIG. 5 and Table 5, the CPP of SEQ ID NO: 1 conjugated to Smn PMO elicits very little GFAP expression, no higher than PMO alone at 5 days and far lower than a competitor CPP Pip6a. Thus, the peptide described in SEQ ID NO: 1 is deemed to be non-toxic in vivo when administered intravitreally at clinically relevant concentrations.

TABLE 3

Efficacy results of CPP enhanced delivery of Smn antisense oligonucleotide in vivo (RPE/choroid)

| SEQ ID NO: | Sequence | Percent exon7-skipped SMN1 transcript (±SD) | |
| --- | --- | --- | --- |
| | | 5 days (±SD) | 7 days (±SD) |
| 1[azk]2 | rrsrtaraGrpGrnssrpsapr[azk]ACTTTCCTTCTTTTTT ATTTTGTCT | 13.05 (±5.14) | 12.22 (±3.61) |
| 2 | ACTTTCCTTCTTTTTTATTTGTCT | 0.00 (±0.00) | 0.00 (±0.00) |
| 3[azk]2 | RXRRBRRXRYQFLIRXRBRXRB[azk]ACTTTCCTTCTTTTTT ATTTTGTCT | 9.94 (±3.99) | 6.70 (±6.35) |

TABLE 4

Efficacy results of CPP enhanced delivery of Smn antisense oligonucleotide in vivo (retina)

| SEQ ID NO: | Sequence | Percent exon7-skipped SMN1 transcript (±SD) | |
| --- | --- | --- | --- |
| | | 5 days (±SD) | 28 days (±SD) |
| 1 [azk]2 | rrsrtaraGrpGrnssrpsapr[azk]ACTTTCCTTCTTTTTT ATTTTGTCT | 19.61 (±7.26) | 13.71 (±10.86) |
| 2 | ACTTTCCTTCTTTTTTATTTGTCT | 0.00 (±0.00) | 0.77 (±1.33) |
| 3[azk]2 | RXRRBRRXRYQFLIRXRBRXRB[azk]ACTTTCCTTCTTTTTT ATTTTGTCT | 21.66 (±11.44) | 3.39 (±2.94) |

TABLE 5

Viability results of CPP enhanced delivery of Smn antisense oligonucleotide in vivo (GFAP)

| SEQ ID NO: | Sequence | GFAP score (±SD) 5 days (±SD) |
| --- | --- | --- |
| 1 [azk]2 | rrsrtaraGrpGrnssrpsapr[azk]ACTTTCCTTCTTTTTTATTTTGTCT | 0.0324 (±0.0095) |
| 2 | ACTTTCCTTCTTTTTTATTTGTCT | 0.0262 (±0.0052) |
| 3[azk]2 | RXRRBRRXRYQFLIRXRBRXRB[azk]ACTTTCCTTCTTTTTTATTTTGTCT | 0.1637 (±0.0911) |

REFERENCES

Verdurmen W P R, Thanos M, Ruttekolk I R, Gulbins E, Brock R. Cationic cell-penetrating peptides induce ceramide formation via acid sphingomyelinase: implications for uptake. J Control Release. 2010; 147:171-179. doi: 10.1016/j.jconrel.2010.06.030.

Zakeri, B.; Fierer, J. O.; Celik, E.; Chittock, E. C.; Schwarz-Linek, U.; Moy, V. T.; Howarth, M. Peptide tag forming a rapid covalent bond to a protein, through engineering a bacterial adhesin. Proc. Natl. Acad. Sci. USA 2012, 109, E690—E697

Milech, N.; Longville, B. A. C.; Cunningham, P. T.; Scobie, M. N.; Bogdawa, H. M.; Winslow, S.; Anastasas, M.; Connor, T.; Ong, F.; Stone, S. R.; et al. GFP-complementation assay to detect functional CPP and protein delivery into living cells. Sci. Rep. 2015, 5, 18329.

Stone, S. R. et al. β-Lactamase tools for establishing cell internalization and cytosolic delivery of cell penetrating peptides. Biomolecules 8, 51-62 (2018).

Hoffmann K, Milech N, Juraja S M, Cunningham P T, Stone S R, Francis R W, Anastasas M, Hall C M, Heinrich T, Bogdawa H M, Winslow S, Scobie M N, Dewhurst R E, Florez L, Ong F, Kerfoot M, Champain D, Adams A M, Fletcher S, Viola H M, Hool L C, Connor T, Longville B A C, Tan Y F, Kroeger K, Morath V, Weiss G A, Skerra A, Hopkins R M, Watt P M. A platform for discovery of functional cell-penetrating peptides for efficient multi-cargo intracellular delivery. Sci Rep. 2018 Aug. 22; 8(1): 12538. doi: 10.1038/s41598-018-30790-2. PMID: 30135446; PMCID: PMC6105642.

Guidotti G, Brambilla L, Rossi D. Cell-penetrating peptides: from basic research to clinics. Trends Pharmacol Sci. 2017; 38:406-424. doi: 10.1016/j.tips.2017.01.003.

van den Berg A, Dowdy S F. Protein transduction domain delivery of therapeutic macromolecules. Curr Opin Biotechnol. 2011; 22:888-893. doi: 10.1016/j.copbio.2011.03.008.

Erazo-Oliveras A, et al. Protein delivery into live cells by incubation with an endosomolytic agent. Nat Methods. 2014; 11:861-867. doi: 10.1038/nmeth.2998.

Wu et al. Cell-penetrating peptides as transporters for morpholino oligomers: effects of amino acid composition on intracellular delivery and cytotoxicity, Nucleic Acids Research, 2007, Vol. 35, No. 15: 5182-5191 doi:10.1093/nar/gkm478

Singh N N, Seo J, Rahn S J, Singh R N (2012) A Multi-Exon-Skipping Detection Assay Reveals Surprising Diversity of Splice Isoforms of Spinal Muscular Atrophy Genes. PLoS One 7(11): e49595. https://doi.org/10.137/journal.pone.0049595

Summerton, J. & Weller, D., 1997. Morpholino antisense oligomers: design, preparation, and properties. Antisense & nucleic acid drug development, 7(3), pp. 187-195

Moulton, H. M. et al., 2004. Cellular uptake of antisense morpholino oligomers conjugated to arginine-rich peptides. Bioconjugate chemistry, 15(2), pp. 290-299.

Dommerholt, J., Rutjes, F. P. J. T. & Delft, F. L., 2016. Strain-Promoted 1,3-Dipolar Cycloaddition of Cycloalkynes and Organic Azides. Topics in Current Chemistry, 374(2), pp. 1-20.

Agard, N. J., Prescher, J. A. & Bertozzi, C. R., 2004. A strain-promoted [3+2] azide-alkyne cycloaddition for covalent modification of biomolecules in living systems. Journal of the American Chemical Society, 126(46), pp. 15046-15047

Roman C. Hillig, Brice Sautier, Jens Schroeder, Dieter Moosmayer, André Hilpmann, Christian M. Stegmann, Nicolas D. Werbeck, Hans Briem, Ulf Boemer, Joerg Weiske, Volker Badock, Julia Mastouri, Kirstin Petersen, Gerhard Siemeister, Jan D. Kahmann, Dennis Wegener, Niels Bohnke, Knut Eis, Keith Graham, Lars Wortmann, Franz von Nussbaum, and Benjamin Bader PNAS Feb. 12, 2019 116 (7) 2551-2560; first published Jan. 25, 2019 https://doi.org/10.1073/pnas.1812963116

Leshchiner E S, Parkhitko A, Bird G H, Luccarelli J, Bellairs J A, Escudero S, Opoku-Nsiah K, Godes M, Perrimon N, Walensky L D. Direct inhibition of oncogenic KRAS by hydrocarbon-stapled SOS1 helices. Proc Natl Acad Sci USA. 2015 Feb. 10; 112(6):1761-6. doi: 10.1073/pnas.1413185112. Epub 2015 Jan. 26. PMID: 25624485; PMCID: PMC4330742.

Shanshan Gu, Danrui Cui, Xiaoyu Chen, Xiufang Xiong, and Yongchao Zhao, PROTACs: An Emerging Targeting Technique for Protein Degradation in Drug Discovery, BioEssays, 40(4), 2018, https://doi.org/10.1002/bies.201700247

K. M. Sakamoto, K. B. Kim, A. Kumagai, F. Mercurio, C. M. Crews, R. J. Deshaies, Proc. Natl. Acad. Sci. USA 2001, 98, 8554.

Renata M. S. Terra, Jorge A. Guimaraes, Hugo Verli, Structural and functional behavior of biologically active monomeric melittin, (2007,) Journal of Molecular Graphics and Modelling, 25(6): 767-772

Chandler, R., Tarasenko, T., Cusmano-Ozog, K. et al. Liver-directed adeno-associated virus serotype 8 gene transfer rescues a lethal murine model of citrullinemia type 1. Gene Ther 20, 1188-1191 (2013) doi:10.1038/gt.2013.53

Stone, S. R. et al. β-Lactamase tools for establishing cell internalization and cytosolic delivery of cell penetrating peptides. Biomolecules 8, 51-62 (2018).

Quinonez S C, Thoene J G. Citrullinemia Type I. 2004 Jul. 7 [Updated 2016 Sep. 1]. In: Adam M P, Ardinger H H, Pagon R A, et al., editors. GeneReviews® [Internet]. Seattle (Wash.): University of Washington, Seattle; 1993-2019. Available from: https://www.ncbi.nlm.nih.gov/books/NBK1458/

Flynn L L, Mitrpant C, Pitout I L, Fletcher S, Wilton S D. Antisense Oligonucleotide-Mediated Terminal Intron Retention of the SMN2 Transcript. Mol Ther Nucleic Acids. 2018 Jun. 1; 11:91-102. doi: 10.1016/j.omtn.2018.01.011. Epub 2018 Jan. 31. PMID: 29858094; PMCID: PMC5854547.

Betts, C., Saleh, A. F., Arzumanov, A. A., Hammond, S. M., Godfrey, C., Coursindel, T., et al. (2012). Pip6-PMO, A New Generation of Peptide-oligonucleotide Conjugates With Improved Cardiac Exon Skipping Activity for DMD Treatment. Molecular Therapy—Nucleic Acids, 1, e38-13. http://doi.org/10.1038/mtna.2012.30

The invention claimed is:

1. A non-naturally occurring cell-penetrating peptide (CPP) comprising the amino acid sequence of:
   (i) RRSRTARAGRPGRNSSRPSAPR (SEQ ID NO: 1); or
   (ii) the amino acid sequence of SEQ ID NO: 1 with one conservative amino acid substitution.

2. The non-naturally occurring CPP of claim 1, further comprising one or more of the following modifications: a non-canonical amino acid, a fatty acid, a detectable label, a cholesterol group, or a reactive group.

3. A cell comprising the non-naturally occurring CPP of claim 1.

4. A kit comprising (i) the non-naturally occurring CPP of claim 1 and (ii) instructions for use.

5. A cell comprising the CPP of claim 2.

6. A kit comprising the CPP of claim 1 and (ii) instructions for use.

7. A kit comprising the modified cell of claim 5 and (ii) instructions for use.

8. The non-naturally occurring CPP of claim 1, wherein the amino acid sequence of the CPP consists of SEQ ID NO: 1.

9. The non-naturally occurring CPP of claim 1, comprising the amino acid sequence of SEQ ID NO: 1.

10. The non-naturally occurring cell-penetrating peptide (CPP) of claim 1, wherein each of the amino acid residues of the amino acid sequence are D-amino acid residues.

11. The non-naturally occurring cell-penetrating peptide (CPP) of claim 1, wherein the amino acid sequence comprises the amino acid sequence of SEQ ID NO: 1 and each of the amino acid residues of SEQ ID NO: 1 are D-amino acid residues.

12. The non-naturally occurring cell-penetrating peptide (CPP) of claim 8, wherein each of the amino acid residues of the amino acid sequence are D-amino acid residues.

13. The non-naturally occurring cell-penetrating peptide (CPP) of claim 2, wherein each of the amino acid residues of the amino acid sequence are D-amino acid residues.

* * * * *